US00PP23455P2

(12) United States Plant Patent
Carruth et al.

(10) Patent No.: US PP23,455 P2
(45) Date of Patent: Mar. 12, 2013

(54) GRANDIFLORA ROSE PLANT NAMED 'WEKFUNK'

(50) Latin Name: *Rosa hybrida*
Varietal Denomination: WEKfunk

(75) Inventors: Thomas F. Carruth, Altadena, CA (US); Christian Bédard, Brea, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 13/317,706

(22) Filed: Oct. 26, 2011

(51) Int. Cl.
*A01H 5/00* (2006.01)

(52) U.S. Cl. ..... Plt./131

(58) Field of Classification Search ..... Plt./131
See application file for complete search history.

*Primary Examiner* — Annette Para

(74) *Attorney, Agent, or Firm* — McKee, Voorhees & Sease, P.L.C.

(57) ABSTRACT

A new variety of Grandiflora rose suitable for garden decoration, having flowers of cream and cherry blushed burgundy coloration.

1 Drawing Sheet

Classification: The present invention relates to a new *Rosa hybrida* plant.

Variety denomination: The new plant has the varietal denomination 'WEKfunk'.

BACKGROUND OF THE INVENTION

This invention relates to a new and distinct variety of Grandiflora Rose. It has as its seed parent the variety known as 'WEKroalt' (U.S. Plant Pat. No. 11,518) and an unknown seedling as its pollen parent.

SUMMARY OF THE INVENTION

Among the features which distinguish the new variety from other presently available and commercial rose cultivars known to the inventors are the following combinations of characteristics: its unusual cream and cherry blushed burgundy flower coloration, its abundant blooms on long cutting stems and its tall upright moderately spreading growing habit. The plant has an upright moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKfunk' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'WEKroalt' by the following combination of characteristics: whereas 'WEKfunk' bears double flowers (about 15 to 22 petals) of cream and cherry blushed burgundy coloration, 'WEKroalt' bears semi-double flowers of irregularly striped and flecked red and white coloration with significantly lesser petalage (about 8 to 12 petals). The new variety is classified as a grandiflora rose with an upright moderately spreading tall growing habit (about 180 to about 200 cm. in height and about 90 to about 105 cm. spread at the widest point), whereas the seed parent is classified as a climbing rose with a spreading significantly taller and wider growing habit (with canes of about 250 to about 360 cm. in length).

The pollen parent is unknown.

COMPARISON WITH THE CLOSEST COMMERCIALLY AVAILABLE CULTIVAR

The new variety may be distinguished from its closest commercially available cultivar, 'MEIsponge' (U.S. Plant Pat. No. 12,802) by the following combination of characteristics: whereas 'WEKfunk' bears double flowers (about 15 to 22 petals), 'MEIsponge' bears double flowers with significantly heavier petalage (commonly approximately 35 petals on average). The new variety has an upright moderately spreading tall growing habit (about 180 to about 200 cm. in height), whereas the closest commercially available cultivar has a rounded significantly shorter growing habit (about 70 to about 80 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of September. Phenotypic expression may vary with environmental, cultural and climatic conditions, as well as differences in conditions of light and soil.

FLOWER

The new variety usually bears its flowers singly, sometimes in clusters of two to four per stem. Flowers may be borne in regular rounded clusters on strong medium to long stems (about 18 to about 72 cm.). Outdoors, the plant blooms very abundantly and nearly continuously during the growing season. The flowers have a slight tea to fruity fragrance.

BUD

The peduncle is about 3.3 to about 5.7 cm. in length, of average caliper (about 0.3 to about 0.5 cm. in diameter), and usually erect. It is almost entirely smooth, with very few stipitate glands and some hairs. Peduncle color is between 146B and 146C often moderately suffused, especially on the side exposed to the sun, with between 187B and 183B.

Before the calyx breaks, the bud is about 1.2 to about 1.7 cm. in diameter at the widest point, about 1.5 to about 2.2 cm. in length, and pointed to somewhat ovoid in shape. The surface of the bud bears between 9 to 12 foliaceous appendages, some stipitate glands and hairs, usually with stout much cut foliaceous parts extending beyond the tip of the bud about ¾ or more of its length. Bud color is between 146A and 146C often moderately suffused, especially on the side exposed to the sun, with between 187B and 183B.

The sepals are about 2.5 to about 3.2 cm. in length and about 0.7 to about 1.0 cm. in width at the widest point. The outer surface color of the sepal is between 146A and 146C often moderately suffused, especially on the side exposed to the sun, with between 187B and 183B. The inner surface color of the sepal is near 146C broadly bordered by near 137A. After the sepals open, the inner surface color is often heavily suffused, especially on the area exposed to the sun, with between 187A and 187B. The inner surface of the sepal is covered with fine wooly tomentum; sepal margins are lined with some stipitate glands and many hairs.

The receptacle of the flower is of moderately short length (about 0.5 to about 0.7 cm.) and average in caliper (about 0.7 to about 0.9 cm. in diameter). The receptacle is urn-shaped in form. Its surface is very smooth with some hairs and with somewhat thin fleshy walls. The receptacle color is between 144A and 146A.

As the petals open (after the calyx breaks), the bud is about 1.7 to about 2.2 cm. in diameter at the widest point, about 2.1 to about 2.7 cm. in length, and pointed to moderately ovoid in form. The color of the under surfaces of the newly opened petals is between 18A and 16C often heavily blushed with between 187B and 45A to as dark as 187A. At the point where the petal attaches, there is a moderately small zone of between 1C and 154C. The color of the upper surfaces of the newly opened petals is between 19B and 20C sometimes lightly streaked with near 53C in the middle of the petal and blushed with between 187A and 187B toward the petal edge. At the point where the petal attaches, there is a very large zone of between 2C and 1C.

BLOOM

When fully open, the bloom ranges from about 8.0 to about 10.6 cm. in diameter. Petalage is double with about 15 to 22 petals and about 2 to 7 petaloids irregularly arranged. When partially open, the bloom form is high centered to somewhat ovoid, and the petals are moderately tightly spiraled to cupped with petal edges moderately reflexed outward. When fully open, the bloom form is cupped, and the petals are loosely cupped to undulated with petal edges very reflexed to somewhat rolled outward.

PETALS

The substance of the petals is moderately heavy and of medium thickness, with upper surfaces moderately satiny to somewhat velvety near the petal edge and under surfaces slightly shiny. The petals are about 2.9 to about 5.2 cm. in length and about 2.9 to about 5.7 cm. in width at the widest point. Petal margins are entire.

The outer and inner petals are moderately obovate to nearly round in shape with rounded apices.

Petaloids are about 2.4 to about 2.9 cm. in length and about 1.1 to about 1.7 cm. in width at the widest point. Petaloids are irregularly shaped moderately obovate to somewhat oblanceolate with rounded apices.

NEWLY OPENED FLOWER

The color at the base of the under surfaces of the outer petals is near 4D gradually suffusing toward the middle of the petal with between 155A and 155D often heavily suffused with between 60D and 45B to as dark as between 187B and 60A. There is no visible change in coloration at the point where the petal attaches. The upper surface color of the outer petals is between 155A and 155B often heavily suffused with between 61C and 45B and blushed mostly toward the edge of the petal with between 60A and 45B to as dark as between 187A and 187B. At the point where the petal attaches, there is a moderately small zone of between 9C and 8B.

The color at the base of the under surfaces of the intermediate and inner petals is between 10A and 13B gradually suffusing toward the middle of the petal with between 36D and 155D often lightly suffused with between 60D and 45B. There is no visible change in coloration at the point where the petal attaches. The upper surface color of the intermediate and inner petals is between 36D and 155B often moderately streaked with near 61C in the middle of the petal and blushed with between 61C and 45B to as dark as between 61B and 59B toward the petal edge. At the point where the petal attaches, there is a very large zone of near 9B.

The under and upper surface colors of the petaloids are similar in coloration to the upper and under surfaces of the intermediate and inner petals.

The general tonality of the newly opened flower is between 36D and 155B often moderately streaked with near 61C in the middle of the petal and blushed with between 61C and 45B to as dark as between 61B and 59B toward the petal edge.

THREE-DAY-OLD FLOWER

The under surface color of the outer, intermediate and inner petals is between 155B and 155D often heavily suffused with between 61C and 45B to as dark as between 61B and 60A. At the point where the petal attaches, there is a small zone of near 10B. The upper surface color of the outer, intermediate and inner petals is between 155B and 155D often heavily suffused with between 61 C and 64C and blushed mostly toward the petal edge with between 60A and 45B to as dark as between 187A and 187B. At the point where the petal attaches, there is a moderately small zone of near 8B.

The under and upper surface colors of the petaloids are similar in coloration to the upper and under surfaces of the intermediate and inner petals.

The general tonality of the three-day-old flower is between 155B and 155D often heavily suffused with between 61C and 64C and blushed mostly toward the petal edge with between 60A and 45B to as dark as between 187A and 187B.

On the spent bloom, the petals usually drop off cleanly.

In September in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 150) and are arranged regularly about the pistils; a few are mixed with petaloids. The filaments are of medium to long length (about 0.4 to about 1.5 cm.) most with anthers. Filaments are between 7A and 9A in color often moderately suffused with 53A and 53B. The anthers are moderately large for the class and all open approximately at the same time. Anther color when immature is near 22A on the external part and near 18D on the internal part. Anther color at maturity is near 162A on the external part and near 200B on the internal part. Pollen is moderately abundant and between 21B and 20A in color.

FEMALE REPRODUCTIVE ORGANS

Pistils vary in number (average about 105). The styles are somewhat uneven, moderately short to average in length (about 0.4 to about 0.8 cm.), thin in caliper and loosely bunched to somewhat separated. Stigma color is between 21D and 19A. Style color is between 1D and 1C often heavily suffused with between 53B and 53C. Ovaries are usually all enclosed in the calyx.

Hips have not been observed on this variety when grown in Pomona, Calif.

FOLIAGE

The compound leaves are usually comprised of three to seven leaflets and are borne abundantly. The five-leaflet leaves are about 8.9 to about 14.3 cm. in length and about 7.2 to about 12.8 cm. in width at the widest point, moderately leathery to somewhat crisp in texture, and glossy in finish on the upper side and matte in finish on the under side. The terminal leaflets are about 4.1 to about 7.7 cm. in length and about 2.7 to about 5.1 cm. in width at the widest point, shaped ovate with mostly acute to sometimes somewhat obtuse apices and rounded bases. Their margins are usually simply serrate.

The upper surface color of the mature leaf is between 137A and 139A. The under surface color of the mature leaf is between 147B and 146B. The upper surface color of the young leaf is between 146A and 146B, often moderately suffused with between 187B and 183A. The under surface color of the young leaf is between 146B and 137D, often heavily suffused with between 187B and 183A.

The rachis is somewhat light to average in caliper and moderately rough. The upper side is deeply grooved with few hairs and some stipitate glands on the edges of the grooves. The under side of the rachis is moderately rough with few stipitate glands and small prickles. The rachis color is near 145A on the under side and near 146A on the upper side often heavily suffused on the young leaf with between 187B and 183A.

The stipules are about 0.9 to about 1.5 cm. in length and moderately wide (about 0.4 to about 0.6 cm.) with somewhat long straight points that usually turn out at an angle of more than 45 degrees. The under and upper surface color of the stipule is between 146A and 137C often heavily suffused on the young leaf with between 187B and 183A.

The petiole is somewhat light to average in caliper and moderately rough. The upper side is deeply grooved with few hairs and some stipitate glands on the edges of the grooves. The under side of the petiole is moderately rough with few stipitate glands and small prickles. The petiole is about 0.8 to about 1.6 cm. in length and about 0.1 to about 0.2 cm in width at the widest point. The petiole color is near 145A on the under side and near 146A on the upper side often heavily suffused on the young leaf with between 187B and 183A.

The plant displays an above average degree of resistance to powdery mildew and rust as compared to other commercial varieties grown under comparable conditions in Pomona, Calif. The plant's winter hardiness and drought/heat tolerance are yet to be determined.

GROWTH

The plant has an upright moderately spreading tall growing habit (about 180 to about 200 cm. in height and about 90 to about 105 cm. spread at the widest point), with full branching. It displays very vigorous growth and the canes are of moderately heavy caliper for the class (about 1.5 to about 2.1 cm. in diameter at the widest point).

The color of the major stems is between 152A and 146B. They bear many large prickles that are about 0.7 to about 1.1 cm. in length. The large prickles are angled slightly downward with a somewhat short broad oval base; prickle color is between 165B and 164A often moderately suffused with near 198D. The major stem bears few small prickles of similar shape and coloration.

The color of the branches is between 146B and 148A. They bear some large prickles which are of similar shape to the large prickles on the major stems. The prickles are about 0.6 to about 0.8 cm. in length. The prickle color is between 152D and 161A sometimes lightly suffused with between 187C and 187D. The branches bear few small prickles of similar shape and coloration.

The color of the new shoots is between 146B and 147C often heavily suffused with between 187B and 183B. They bear some large prickles which are of similar size and shape to the large prickles on the branches; prickle color is between 152D and 161A often heavily suffused with between 187C and 183C. The shoots bear few small prickles of similar shape and coloration.

We claim:

1. A new and distinct Grandiflora rose plant of the variety substantially as described and illustrated herein.

* * * * *

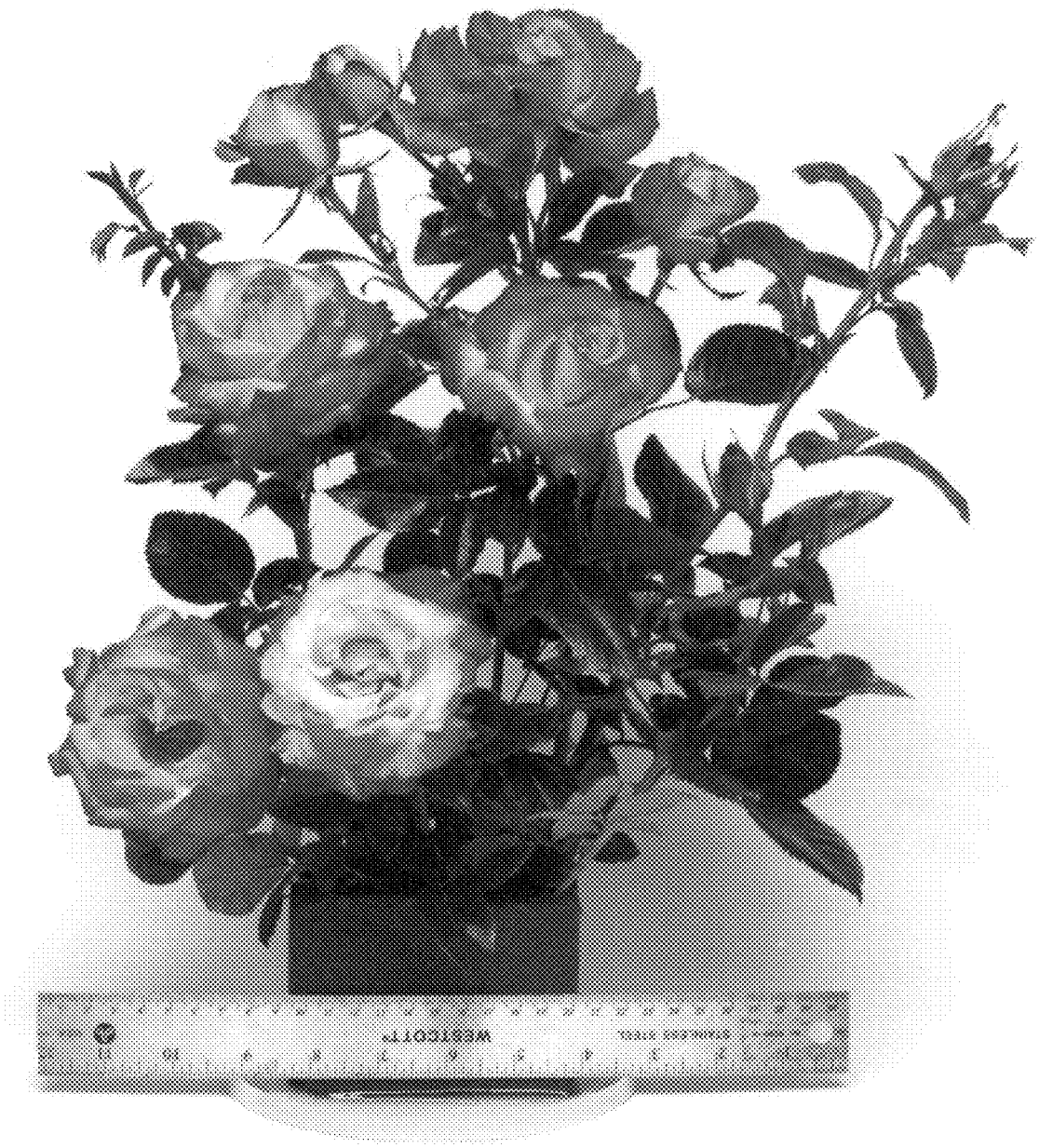
WEATGOTTE